United States Patent [19]

Brand et al.

[11] Patent Number: 4,806,638

[45] Date of Patent: Feb. 21, 1989

[54] NEUTRALIZATION OF REACTION MIXTURES OBTAINED BY BECKMAN REARRANGEMENT OF CYCLOHEXANONE OXIME

[75] Inventors: Uwe Brand, Lampertheim; Ruediger Schmitz, Lambsheim; Ernst Deuker, Gruenstadt; Hugo Fuchs, Ludwigshafen, all of Fed. Rep. of Germany

[73] Assignee: BASF Aktiengesellschaft, Ludwigshafen, Fed. Rep. of Germany

[21] Appl. No.: 109,405

[22] Filed: Oct. 19, 1987

[30] Foreign Application Priority Data

Oct. 17, 1986 [DE] Fed. Rep. of Germany ....... 3635363

[51] Int. Cl.⁴ .................... C07D 201/16; C01B 1/242
[52] U.S. Cl. ..................................... 540/540; 423/549
[58] Field of Search ......................................... 540/540

[56] References Cited

U.S. PATENT DOCUMENTS 2,605,261 7/1952 Kahr et al. ........................ 540/540
4,138,472 2/1979 Neubauer et al. ................. 540/540

FOREIGN PATENT DOCUMENTS 996322 6/1965 United Kingdom ................ 540/540

Primary Examiner—Robert T. Bond
Attorney, Agent, or Firm—Keil & Weinkauf

[57] ABSTRACT

Reaction mixtures obtained by Beckmann rearrangement of cyclohexanone oxime with sulfuric acid or oleum are neutralized by a process which comprises the following steps:
(a) mixing the reaction mixture with recycled ammonium sulfate mother liquor whose concentration is chosen so that no solid ammonium sulfate is precipitated during the neutralization,
(b) neutralization by feeding gaseous ammonia which contains water or an aqueous ammonium sulfate solution in finely divided liquid form through a plurality of nozzle orifices into the solution of the reaction mixture in the ammonium sulfate mother liquor at elevated temperatures,
(c) separation of crude lactam from the aqueous ammonium sulfate solution,
(d) evaporation of the ammonium sulfate solution under reduced pressure and with separation of the crystalline ammonium sulfate from the ammonium sulfate mother liquor and
(e) recycling of the ammonium sulfate mother liquor to stage a).

8 Claims, No Drawings

NEUTRALIZATION OF REACTION MIXTURES OBTAINED BY BECKMAN REARRANGEMENT OF CYCLOHEXANONE OXIME

The Beckmann rearrangement reaction of cyclohexanone oxime with sulfuric acid or oleum gives a reaction mixture which essentially consists of crude caprolactam (crude lactam) and sulfuric acid. Such reaction mixtures are neutralized with ammonia, and crude lactam and solid ammonium sulfate are separated off. German Published Application DAS No. 2,651,195 describes a process in which the reaction mixture from the Beckmann rearrangement reaction is worked up by neutralization with ammonia at elevated temperatures with the addition of recycled ammonium sulfate mother liquor, the concentration being chosen so that no solid ammonium sulfate is precipitated during the neutralization, separation of the crude caprolactam from the ammonium sulfate solution, crystallization of ammonium sulfate by evaporation of the ammonium sulfate solution under reduced pressure, removal of the crystalline ammonium sulfate and recycling of the mother liquor to the neutralization stage. In this procedure, the neutralization may be effected with gaseous ammonia or ammonia in aqueous solution or together with ammonium sulfate mother liquor, and the ammonia can be combined with the ammonium sulfate solution either upstream of the neutralization stage or directly in the neutralization stage. In the neutralization with itroduction of gaseous ammonia through a plurality of nozzel orifices, it has been found that these orifices become blocked within a short time, and uniform feed of ammonia into the medium to be neutralized, and hence satisfactory neutralization of the said medium, are not ensured.

It is an object of the present invention to provide a process for the neutralization of reaction mixtures from the Beckmann rearrangement reaction, in which gaseous ammonia is fed in during the neutralization without difficulties and uniform neutralization of the reaction mixture is ensured.

We have found that this object is achieved by a process for the neutralization of reaction mixtures obtained by Beckmann rearrangement of cyclohexanone oxime with sulfuric acid or oleum, which comprises the following steps:
(a) mixing the reaction mixture with recycled ammonium sulfate mother liquor whose concentration is chosen so that no solid ammonium sulfate is precipitated during the neutralization,
(b) neutralization by feeding in gaseous ammonia at elevated temperatures,
(c) separation of crude lactam from the aqueous ammonium sulfate solution,
(d) evaporation of the ammonium sulfate solution under reduced pressure and with separation of the crystalline ammonium sulfate from the ammonium sulfate mother liquor and
(e) recycling of the ammonium sulfate mother liquor to stage (a),
wherein gaseous ammonia which contains water or an aqueous ammonium sulfate solution in finely divided liquid form is fed through a plurality of nozzle orifices into the solution of the reaction mixture in ammonium sulfate mother liquor.

The novel process has the advantage that no blockages occur while gaseous ammonia is being fed in and, in addition, uniform neutralization of the solution of the reaction mixture in the ammonium sulfate mother liquor is ensured.

The starting materials used are reaction mixtures obtained by Beckmann rearrangement of cyclohexanone oxime with sulfuric acid or oleum. Typical mixtures contain from 40 to 50% by weight of caprolactam and from 50 to 60% by weight of sulfuric acid. In stage (a), the reaction mixture is first mixed with recycled ammonium sulfate mother liquor whose concentration is chosen so that no solid ammonium sulfate is precipitated during the neutralization. The concentration of the ammonium sulfate mother liquor used is therefore chosen no higher than the concentration required to give an almost saturated solution after the neutralization. If a temperature increase of 10°–40° C. is envisaged during the neutralization, it is advantageous to use from 5 to 50 times the amount, based on the mixture from the rearrangement reaction, of ammonium sulfate mother liquor. A suitable concentration is advantageously obtained if the ammonium sulfate mother liquor is diluted beforehand, in particular in a ratio qf mother liquor to water of from 5:1 to 65:1. A suitable ammonium sulfate mother liquor has, for example, a concentration of 35 to 45% by weight.

In stage (b), the neutralization is carried out by feeding in gaseous ammonia at elevated temperatures. Gaseous ammonia is introduced into the solution of the reaction mixture in the ammonium sulfate mother liquor through a plurality of nozzle orifices, for example from 50 to 2,000 nozzle orifices per m$^2$, the orifices having a diameter of from 1 to 5 mm. The feed is advantageously effected in a mixing tube in order to ensure rapid mixing and hence neutralization. A pH of from 3 to 6, in particular from 4.5 to 5.0, is advantageously maintained in the neutralization zone. The neutralization is advantageously carried out at from 80° to 115° C. In this case, the pressure is advantageously the autogenous pressure at the particular neutralization temperature and composition of the neutralized mixture.

According to the invention, water or an aqueous ammonium sulfate solution, for example having a concentration of up to 35, preferably from 20 to 30% by weight of ammonium sulfate, in finely divided liquid form, is added to the gaseous ammonia before the latter is fed in. This is advantageously effected by spraying the stated media into the ammonia gas stream by means of a spray nozzle, a mean drop size of from 0.2 to 2.0 mm advantageously being produced. Not less than 0.05 l of water or not less than 0.1 l of aqueous ammonium sulfate solution is advantageously used per m$^3$ of gaseous ammonia at about 25° C. From 0.05 to 0.5 l, in particular from 0.05 to 0.25 l, of water per m$^3$ of gaseous ammonia or from 0.1 to 1.0 l, in particular from 0.1 to 0.5 l, of ammonium sulfate solution per m$^3$ of gaseous ammonia has proven particularly useful.

In stage (c), the neutralized mixture is then passed into a separation zone where the two liquid phases, the crude lactam and the aqueous ammonium sulfate solution, are separated. This separation can be carried out, for example, after separation into two layers by simply decanting or using separators. Of course, the autogenous pressure is advantageously maintained.

The light phase contains the aqueous crude lactam, which is advantageously cooled in order to avoid the formation of byproducts. This phase is then extracted with benzene, and caprolactam is obtained from the benzene solution.

The ammonium sulfate solution separated off in the separation zone is advantageously fed, without being cooled, to an evaporator crystallization stage (d), where an ammonium sulfate mother liquor is obtained under reduced pressure and with separation of the crystalline ammonium sulfate. Evaporation is advantageously effected under from 200 to 800 mbar. In this procedure, water is evaporated until the ammonium sulfate solution advantageously reaches 72°–101° C. Ammonium sulfate crystallizes out as a result of supersaturation. Of course, evaporation is effected not completely but always only to such an extent that the amount of ammonium sulfate which crystallizes out is the same as that formed during the neutralization. The amount of water to be evaporated is also based on this principle. The resulting salt slurry is fed to a separating apparatus, for example a filter or a centrifuge.

This procedure gives an ammonium sulfate mother liquor which, in stage (e), is recycled to stage (a). Of course, water is advantageously added to the ammonium sulfate mother liquor in an amount which corresponds to the amount of water evaporated. The condensate of the vapors removed from the evaporator or crystallizer is advantageously used for this purpose. The amount of water separated off with the lactam should also be replaced. In any case, the amount of water added must be sufficient to prevent precipitation of ammonium sulfate during the neutralization. Because the solubility of ammonium sulfate is temperature-dependent, the minimum amount of water for dilution depends on the temperature reached during the neutralization and on the desired concentration of the ammonium sulfate solution. In general, from 1 to 1.5 parts of water for dilution are sufficient per part of ammonium sulfate expected.

The Examples which follow illustrate the process according to the invention. Parts by weight bear the same relation to parts by volume as that of the kilogram to the liter.

EXAMPLE 1

12.4 parts of a sulfuric acid-containing mixture from the rearrangement of cyclohexanone oxime (consisting of 42.7% by weight of caprolactam and 57.3% by weight of sulfuric acid) are first mixed, in a circulation, with 200 parts/hour of an ammonium sulfate solution having a concentration of 42.5% by weight, and the mixture is passed through a mixing tube in which 3,220 parts by volume of gaseous ammonia are fed in via 1,200 nozzles of 4 mm diameter. 0.13 l of water per cubic meter of ammonia gas is fed in the gaseous ammonia by means of a spray nozzle under a differential pressure of 2 bar, drops having a mean diameter of 1 mm being formed. In the neutralization zone, the temperature increases from 90° C. to 100° C. and the resulting pH is 4.5. The autogenous pressure is 1 bar. The neutralization mixture is then passed into a separation vessel, in which 3.80 parts/hour of aqueous crude caprolactam containing about 68% by weight of caprolactam, as the light phase, and 209.5 parts of concentrated ammonium sulfate solution, as the heavy phase, are separated from one another. The concentrated ammonium sulfate solution is passed into a crystallizer/evaporator, and 4.8 parts/hour are evaporated under 540 mm Hg. During this procedure, the solution cools to 90° C., supersaturation and crystallization occurring. 4.7 parts of ammonium sulfate are separated off from the resulting salt slurry in a centrifuge. 200 parts/hour of ammonium sulfate mother liquor remain and are again diluted with 4.8 parts of water and recycled to stage (a). After an operating time of 30 days, the feed orifices for the gaseous ammonia still remain free of blockages.

EXAMPLE 2

The procedure described in Example 1 is followed, and 0.26 l of 23% strength by weight aqueous ammonium sulfate solution per $m^3$ of ammonia gas is fed into the gaseous ammonia by means of a spray nozzle under a differential pressure of 2 bar. During an operating time of 30 days, no blockage of the feed orifices for the gaseous ammonia is observed.

COMPARATIVE EXAMPLE 1

The procedure described in Example 1 is followed, and gaseous ammonia is fed through the nozzle orifices, but without the addition of any further substances. After only a few minutes, the pressure in the feed line for gaseous ammonia begins to increase and after a short time the plant has to be shut down since the orifices for ammonia feed are blocked with ammonium sulfate which has crystallized out.

COMPARATIVE EXAMPLE 2

The procedure described in Example 1 is followed, except that 200 g of water in the form of steam at 120° C. are added, per $M^3$ of ammonia, to the ammonia gas stream. The plant has to be shut down after 0.5 hour since the feed orifices for the gaseous ammonia become blocked by ammonium sulfate which crystallizes out.

We claim:

1. A process for the neutralization of a reaction mixture obtained by Beckmann rearrangement of cyclohexanone oxime with sulfuric acid or oleum, which comprises the following steps:
   (a) mixing the reaction mixture with recycled ammonium sulfate mother liquor whose concentration is chosen so that no solid ammonium sulfate is precipitated during the neutralization,
   (b) neutralization by feeding gaseous ammonia which contains water or an aqueous ammonium sulfate solution in finely divided liquid form through a plurality of nozzle orifices into the solution of the reaction mixture in the ammonium sulfate mother liquor at elevated temperatures,
   (c) separation of crude lactam from the aqueous ammonium sulfate solution,
   (d) evaporation of the ammonium sulfate solution under reduced pressure and with separation of the crystalline ammonium sulfate from the ammonium sulfate mother liquor and
   (e) recycling of the ammonium sulfate mother liquor to stage (a).

2. A process as claimed in claim 1, wherein in stage (a), the reaction mixture is mixed with from 5 to 50 times the amount of recycled ammonium sulfate mother liquor.

3. A process as claimed in claim 1, wherein not less than 0.05 $l/m^3$ of water or not less than 0.1 $l/m^3$ of aqueous ammonium sulfate solution in finely divided liquid form is added to the gaseous ammonia.

4. A process as claimed in claim 1, wherein the gaseous ammonia contains water or aqueous ammonium sulfate solution in a droplet size of from 0.2 to 2.0 mm.

5. A process as claimed in claim 1, wherein the neutralization is carried out at from 80° to 115° C. under autogenous pressure.

6. A process as claimed in claim 1, wherein the neutralization is carried out up to a pH of from 3 to 6.

7. A process as claimed in claim 1, wherein the ammonium sulfate solution is evaporated in stage (d) under from 200 to 800 mbar with cooling to 72°–101° C.

8. A process as claimed in claim 1, wherein water is added to the ammonium sulfate mother liquor in a ratio of mother liquor to water of from 5:1 to 65:1 before the mother liquor is recycled to stage (a).

* * * * *